United States Patent [19]

Bellis

[11] Patent Number: 4,543,424
[45] Date of Patent: Sep. 24, 1985

[54] PROCESS FOR PREPARING SUBSTITUTED FORMAMIDES

[75] Inventor: Harold E. Bellis, Wilmington, Del.

[73] Assignee: E. I. Du Pont de Nemours and Company, Wilmington, Del.

[21] Appl. No.: 598,184

[22] Filed: Apr. 9, 1984

[51] Int. Cl.[4] ............................................. C07C 102/00
[52] U.S. Cl. ..................................... 564/215; 564/218; 564/219; 260/239 A; 260/239 B; 544/386; 546/245
[58] Field of Search ....................... 564/215, 218, 219; 260/239 A, 239 B; 544/386; 546/245

[56] References Cited

U.S. PATENT DOCUMENTS

| | | | |
|---|---|---|---|
| 3,483,210 | 12/1969 | Rosenblatt et al. | 564/215 X |
| 4,042,621 | 8/1977 | Sauer | 260/561 R |
| 4,281,193 | 7/1981 | Bellis | 564/215 |
| 4,329,462 | 5/1982 | Tamura et al. | 564/215 X |

Primary Examiner—Paul F. Shaver

[57] ABSTRACT

In the process of preparing substituted formamides by the catalytic oxidation of substituted tertiary amines, in which a metal halide catalyst is used in conjunction with an alkali metal halide corrosion inhibitor, pitting of equipment can be inhibited by including in the reaction medium a primary alkylamine, urea or a substituted urea, or thiourea or a substituted thiourea.

3 Claims, No Drawings

PROCESS FOR PREPARING SUBSTITUTED FORMAMIDES

DESCRIPTION

1. Technical Field

This invention relates to a process for preparing substituted formamides by the catalytic oxidation of substituted tertiary amines. It is more particularly directed to such a process in which the catalyst is a combination of metal halide and an alkali metal halide or ammonium halide.

2. Background and Summary of the Invention

It is well known that substituted formamides can be prepared from tertiary amines by catalytic oxidation. One such method is shown in U.S. Pat. No. 4,042,621 to Sauer. In that method, a tertiary amine is catalytically oxidized to a corresponding formamide using as the catalyst a soluble metal halide.

The Sauer process is an excellent one. As is well known, however, metal halides are quite corrosive to metals such as stainless steel customarily used in fabricating chemical processing equipment. In my U.S. Pat. No. 4,281,193, I disclose that this corrosiveness can be inhibited by using a metal halide catalyst in conjunction with a chloride, bromide or iodide of sodium, potassium, lithium or ammonium.

I have now found that this corrosion inhibition can be further enhanced, particularly with regard to pitting of metal equipment, by including in the reaction medium an adjunct which is a primary alkylamine, urea or a substituted urea, or thiourea or a substituted thiourea.

DETAILED DESCRIPTION OF THE INVENTION

The oxidative reaction proceeds according to the equation

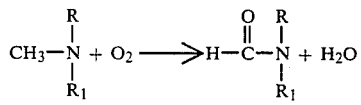

where R and $R_1$ are alkyl radicals of 1-8 carbon atoms, aryl radicals of 6-10 carbon atoms, aralkyl radicals of 7-10 carbon atoms or alkaryl radicals of 7-10 carbon atoms, and $R_1$ can in addition be an alkyl radical containing a $-N(CH_3)R_2$ group in which $R_2$ can be hydrogen, an alkyl radical of 1-8 carbon atoms, an aryl radical of 6-10 carbon atoms, an aralkyl radical of 7-10 carbon atoms or an alkaryl radical of 7-10 carbon atoms, with the provisos that R and $R_1$ can be joined together to form an alkylene or azaalkylene group of 3-8 carbon atoms, and when R is alkyl or aralkyl, $R_1$ can be hydrogen.

The amine used as a starting material in the reaction can be any which satisfies the formula above, and this amine will give the corresponding formamide, as shown by the equation. The oxidation of trimethylamine to dimethylformamide is preferred.

The oxygen used in the process can be pure or mixed with an inert gas or gases such as air. The use of air is preferred.

The reaction is ordinarily conducted in a liquid medium because the medium helps dissolve the catalyst and helps moderate the exothermic reactions which take place. Any organic liquid which is inert to the reaction in the sense that it does not interfere with it can be used. Illustrative are amides such as methylformamide, dimethylformamide and dimethylacetamide; alkanenitriles such as acetonitrile and propionitrile; alkanols such as methanol, ethanol, isopropanol and butanol; and sulfoxides such as dimethylsulfoxide. Dimethylformamide is preferred, especially when it is also the product of the reaction, as this eliminates the need for the additional step of removing extraneous solvent at the end of the process.

The catalyst used in the reaction is a soluble chloride, bromide or iodide of copper, cobalt, gold, iron, mercury, nickel, palladium, platinum, silver or zinc. Mixtures can also be used. The catalysts preferred for use are the copper chlorides, especially $CuCl_2$. "Soluble" in this context means that the catalyst dissolves in the reaction medium, usually completely, but always to the extent that it provides a catalytic effect.

The catalyst is used in conjunction with an alkali metal halide which is a chloride, bromide or iodide of sodium, potassium, lithium or ammonium. Sodium iodide is preferred. Mixtures of alkali metal halides can also be used.

The catalyst and alkali metal halide are used in proportions which are plus or minus 50% of the equimolar amounts. Equimolar amounts are preferred.

The catalyst-metal halide combination is ordinarily present in the reaction mass at a concentration of 0.25-20% by weight. The absolute amount of the combination used is of secondary importance, it being important only that a catalytically effective amount be present.

The adjunct used according to the invention can be a primary alkylamine, urea or a substituted urea, or thiourea or a substituted thiourea.

The primary alkylamines used are those whose alkyl groups contain 4-12 carbon atoms. The substituted ureas and thioureas are those bearing one or more alkyl groups of 1-6 carbon atoms. Thiourea is preferred for use. Mixtures of adjuncts can also be used.

The adjunct is ordinarily present in the reaction mass at a concentration of 0.005-0.3%, by weight, preferably 0.005-0.2%.

The process of the invention can be run batchwise or in a continuous fashion.

In the batch mode, a reactor is charged with a suitable liquid medium into which is dissolved the desired amount of catalyst, alkali metal halide and adjunct. To the resulting medium is then added 20-40%, by weight of the medium, of the amine starting material. The reactor is then sealed and heated to and held at 25°-150° C., preferably 80°-115° C. Enough oxygen or air is introduced into the reactor to give an amine/oxygen mole ratio of 1/1.1-1.2 and to maintain a pressure of 344-690 kPa (50-100 psig) if oxygen is used or 2758-3448 kPa (400-500 psig) if air is used. The reaction mass is then agitated until the reaction is finished, normally a matter of 1-2 hours, as signalled by cessation of oxygen absorption.

The reactor is then cooled to ambient temperature, and unreacted oxygen and unreacted amine are vented. The substituted formamide product can be recovered from the reaction mass by conventional distillation techniques.

The process is run continuously in much the same fashion. A reactor is charged with the liquid medium and the desired amount of catalyst-metal halide-adjunct combination. The reactor is then pressurized with oxygen or air, and the amine and oxygen or air are fed into the reactor in such amounts that the amine/oxygen mole ratio is held within the range of 1/1.05-1.2 and the pressure is maintained at 344-610 kPa if oxygen is used and 2758-3448 kPa if air is used. The temperature of the reactor contents is held within the range 25°-150° C., preferably 80°-115° C., and the residence time of the reaction mass in the reactor is about ½-1 hour, preferably ¾ hour.

The effluent from the reactor is fed to a separator, where the pressure is released and the gases vented. Substituted formamide product is obtained from the remaining liquid by conventional distillation procedures.

When the continuous mode of operation is used, an adjunct whose boiling point is above that of the product remains in the reaction medium in the final separation step and can be easily recycled. The small amount of adjunct lost through purges or evaporation can be easily replaced by simply feeding the required amount into the reaction mass.

An adjunct whose boiling point is below the boiling point of the product is removed with the product and separated from it by fractional distillation, after which it can be recycled to the reaction mass if desired.

EXAMPLE

Those skilled in the art will be able to practice this invention more easily after referring to the following illustrative example.

These artisans will no doubt be able to compose numerous variations on the theme disclosed, such as changing the amounts of components slightly but insignificantly from those shown, adding innocuous substances, or substituting equivalent or nearly equivalent components for those shown. I consider all these variations to be part of my inventive concept.

In the Example, all parts are by weight.

A titanium pressure reactor was filled to 80% of its capacity with a charge of
Dimethylformamide: 98.1 parts
CuCl$_2$: 1.0 part
NaI: 0.9 part
Thiourea: 0.2 part
The charge was heated to and held at a temperature of 115° C., with stirring. The reactor was then sealed and pressurized with air to 3448 kPa (500 psig). Air was continuously fed in to maintain this pressure.

Trimethylamine was then continuously fed into the reactor at a rate which maintained an oxygen/trimethylamine mol ratio of 1/1.08, as determined with flow meters. Residence time of the trimethylamine in the vessel was 45 minutes.

Overflow from the reactor was continuously fed to an enclosed separator, where gases were removed from the top and liquid crude dimethylformamide removed from the bottom.

After 1440 hours of operation, stainless steel coupons (18% chromium, 8% nickel and 74% iron) showed no pitting, as determined by examination under a microscope.

I claim:
1. In the process for catalytically preparing a substituted formamide, which process comprises
   (A) bringing together, in an inert medium, under conditions suitable for reaction,
      (1) a compound represented by the structure

where R and R$_1$ are alkyl radicals of 1-8 carbon atoms, aryl radicals of 6-10 carbon atoms, aralkyl radicals of 7-10 carbon atoms or alkaryl radicals of 7-10 carbon atoms, and R$_1$ can in addition be an alkyl radical containing a —N(CH$_3$)R$_2$ group in which R$_2$ can be hydrogen, an alkyl radical of 1-8 carbon atoms, an aryl radical of 6-10 carbon atoms, an aralkyl radical of 7-10 carbon atoms or an alkaryl radical of 7-10 carbon atoms, with the provisos that R and R$_1$ can be joined together to form an alkylene or azaalkylene group of 3-8 carbon atoms, and when R is alkyl or aralkyl, R$_1$ can be hydrogen;
      (2) oxygen; and
      (3) a catalytically effective amount of a combination of
         (a) a soluble chloride, bromide or iodide of copper, cobalt, gold, iron, mercury, nickel, palladium, platinum, silver or zinc, and
         (b) a chloride, bromide, or iodide of sodium, potassium, lithium or ammonium, and then
   (B) recovering the substituted formamide product from the reaction mass, the improvement comprising including in the medium of (A) an effective amount of an adjunct which is one or more members selected from the group consisting of
      (1) a primary alkylamine whose alkyl group contains 4-12 carbon atoms,
      (2) urea or urea substituted with one or more alkyl radicals of 1-6 carbon atoms, and
      (3) thiourea or thiourea substituted with one or more alkyl radicals of 1-6 carbon atoms.

2. The process of claim 1 wherein the adjunct is thiourea.

3. The process of claim 1 wherein the compound in (A)(1) is trimethylamine, the combination in (A)(3) is of cupric chloride and sodium iodide, and the adjunct is thiourea.

* * * * *